US007893283B2

(12) United States Patent
Naidu (10) Patent No.: US 7,893,283 B2
(45) Date of Patent: Feb. 22, 2011

(54) SEMI-SYNTHESIS OF TAXANE INTERMEDIATES AND THEIR CONVERSION TO PACLITAXEL AND DOCETAXEL

(75) Inventor: Ragina Naidu, Burnaby (CA)

(73) Assignee: Chatham Biotec, Limited, Riverview, New Brunswick (CA)

( * ) Notice: Subject to any disclaimer, the term of this patent is extended or adjusted under 35 U.S.C. 154(b) by 57 days.

(21) Appl. No.: 11/628,428

(22) PCT Filed: Jun. 3, 2005

(86) PCT No.: PCT/US2005/019697
§ 371 (c)(1),
(2), (4) Date: Jan. 18, 2008

(87) PCT Pub. No.: WO2005/118563

PCT Pub. Date: Dec. 15, 2005

(65) Prior Publication Data

US 2008/0262250 A1 Oct. 23, 2008

(51) Int. Cl.
*C07D 305/14* (2006.01)
(52) U.S. Cl. ...................................................... 549/510
(58) Field of Classification Search ................. 514/449; 549/510
See application file for complete search history.

(56) References Cited

U.S. PATENT DOCUMENTS

| 5,319,112 | A | 6/1994 | Kingston et al. |
| 5,380,916 | A | 1/1995 | Rao |
| 5,530,020 | A | 6/1996 | Gunawardana et al. |
| 5,688,977 | A | 11/1997 | Sisti et al. |
| 5,703,247 | A | 12/1997 | Kingston et al. |
| 5,808,113 | A | 9/1998 | Murray et al. |
| 6,136,989 | A | 10/2000 | Foo et al. |
| 6,197,981 | B1 | 3/2001 | Liu |
| 6,222,053 | B1 | 4/2001 | Zamir et al. |
| 0,041,803 | A1 | 11/2001 | Kasitu et al. |
| 6,576,777 | B2 | 6/2003 | Zamir et al. |
| 6,846,937 | B2 | 1/2005 | Erhardt et al. |
| 7,202,370 | B2 | 4/2007 | Naidu |
| 2001/0014746 | A1 | 8/2001 | Holton |
| 2001/0037020 | A1 | 11/2001 | Holton |
| 2008/0033189 | A1 | 2/2008 | Naidu |
| 2008/0146824 | A1 | 6/2008 | Naidu et al. |

FOREIGN PATENT DOCUMENTS

| EP | 1403261 | 3/2004 |
| WO | 98/50378 | 11/1998 |
| WO | 99/54322 | 10/1999 |
| WO | 2004/033442 | 4/2004 |
| WO | 2005/082875 | 9/2005 |
| WO | 2005/105767 | 11/2005 |
| WO | 2006/004708 | 1/2006 |
| WO | 2006/004898 | 1/2006 |

OTHER PUBLICATIONS

Office action from the U.S. Patent and Trademark Office in U.S. Appl. No. 11/587,407, dated Nov. 27, 2009.
Nicolaou et al., "Chemistry and Biology of Taxol," *Angew. Chem. Int. Ed. Engl.* 33:15-44, 1994.
Beckvermit et al., "An Improved Method for Separating Paclitaxel and Cephalomannine Using Ozone and Girard Reagents," *J. Org. Chem.*, vol. 61, No. 25, pp. 9038-9040 (1996).
Chen et al., "Synthesis and Biological Evaluation of Novel C-4 Aziridine-Bearing Paclitaxel (Taxol) Analogs," CAPLUS 123:112445, Abstract Only, *Journal of Medicinal Chemistry*, vol. 38, No. 12, pp. 2263-2267 (1995).
Commerçon et al., "Improved Protection and Esterification of a Precursor of the TAXOTERE® and Taxol Side Chains," *Tetrahedron Letters*, vol. 33, No. 36, pp. 5185-5188 (1992).
Final Office action from the U.S. Patent and Trademark Office in U.S. Appl. No. 11/587,407, dated Apr. 16, 2009.
Final Office action from the U.S. Patent and Trademark Office in U.S. Appl. No. 11/631,466, dated Jul. 20, 2009.
Gennari et al., "Computer-Assisted Design and Synthetic Applications of Chiral Enol Borinates: Novel, Highly Enantioselective Aldol Reagents," *J. Braz. Chem. Soc.*, vol. 9, No. 4, pp. 319-326 (1998).
Gennari et al., "Rationally designed chiral enol borinates: Powerful reagents for the stereoselective synthesis of natural products," *Pure & Appl. Chem.*, vol. 69, No. 3, pp. 507-512 (1997).
International Search Report for PCT/US2005/014080 (mailed Aug. 3, 2005).
International Search Report for PCT/US2005/005953 (mailed Sep. 14, 2005).
International Search Report for PCT/US2005/022844 (mailed Oct. 20, 2005).
International Search Report for PCT/US2005/023224 (mailed Jan. 25, 2006).
Kanazawa et al., "Highly Stereocontrolled and Efficient Preparation of the Protected, Esterification-Ready Docetaxel (Taxotere) Side Chain," *Journal of Organic Chemistry*, vol. 59, pp. 1238-1240 (1994).
Office action from the U.S. Patent and Trademark Office in U.S. Appl. No. 10/590,647, dated Sep. 19, 2008.
Office action from the U.S. Patent and Trademark Office in U.S. Appl. No. 11/587,407, dated Sep. 25, 2008.
Office action from the U.S. Patent and Trademark Office in U.S. Appl. No. 11/631,466, dated Jul. 24, 2008.
Office action from the U.S. Patent and Trademark Office in U.S. Appl. No. 11/631,466, dated Jan. 26, 2009.
Pines et al., "The Stereochemistry of 2,3-Diphenyl-1-methylpropylamine," *Journal of Medical Chemistry*, vol. 10, No. 4, pp. 725-728 (1967).
Rimoldi et al., "An Improved Method for the Separation of Paclitaxel and Cephalomannine," *Journal of Natural Products*, vol. 59, No. 2, pp. 167-168 (1996).
International Search Report for PCT/US2005/019697.
Klein, L., "Synthesis of 9-Dihydrotaxol: A Novel Bioactive Taxane," *Tetrahedron Letters*, vol. 34, No. 13, pp. 2047-2050 (Mar. 26, 1993).
Office Action from European Patent Office in European Patent Application No. 05760288.0, dated Jul. 23, 2009.
Notice of Allowance from the U.S. Patent and Trademark Office in U.S. Appl. No. 11/587,407, dated Jul. 22, 2010.
Office action from U.S. Patent and Trademark Office in U.S. Appl. No. 11/631,466, dated Mar. 12, 2010.

*Primary Examiner*—Shawquia Young
(74) *Attorney, Agent, or Firm*—Klarquist Sparkman, LLP (57) ABSTRACT

A process is provided for the semi-synthesis of taxane intermediates useful in the preparation of paclitaxel and docetaxel, in particular, the semi-synthesis of protected taxane intermediates.

4 Claims, 3 Drawing Sheets

SEMI-SYNTHESIS OF TAXANE INTERMEDIATES AND THEIR CONVERSION TO PACLITAXEL AND DOCETAXEL

CROSS REFERENCE TO RELATED APPLICATIONS

This is the U.S. National Stage of International Application No. PCT/US2005/019697, filed Jun. 3, 2005, which was published in English under PCT Article 21(2), and which claims the benefit of U.S. application Ser. No. 10/862,191, filed Jun. 4, 2004.

BACKGROUND OF THE INVENTION

1. Field of the Invention

The present invention relates to the semi-synthesis of taxane intermediates useful in the preparation of paclitaxel and docetaxel, in particular, the semi-synthesis of protected taxane intermediates.

2. Description of the Related Art

The taxane family of terpenes has received much attention in the scientific and medical community because members of this family have demonstrated broad spectrum anti-leukemic and tumor-inhibitory activity. A well-known member of this family is paclitaxel (1, Taxol).

TAXOL
(1)

Paclitaxel was first isolated from the bark of the pacific yew tree (*Taxus brevifolia*) in 1971, and has proved to be a potent natural anticancer agent. For example, paclitaxel has been found to have activity against different forms of leukemia and against solid tumors in the breast, ovary, brain, and lung in humans.

This activity has stimulated an intense research effort over recent years, including the search for other taxanes having similar or improved properties, and the development of synthetic pathways for making taxanes such as paclitaxel. One result from this research effort was the discovery of a synthetic analog of paclitaxel, docetaxel (2, more commonly known as taxotere). As disclosed in U.S. Pat. No. 4,814,470, taxotere has been found to have very good anti-tumor activity and better bio-availability than paclitaxel. Taxotere is similar in structure to paclitaxel, having t-butoxycarbonyl instead of benzoyl on the amino group at the 3' position, and a hydroxy group instead of the acetoxy group at the C-10 position.

TAXOTERE
(2)

Taxanes are structurally complicated molecules, and the development of commercially viable synthetic methods to make taxanes has been a challenge. A number of semi-synthetic pathways have been developed, which typically begin with the isolation and purification of a naturally occurring material and then its conversion to the taxane of interest. For example, paclitaxel and taxotere may be prepared semi-synthetically from 10-deacetylbaccatin III or baccatin III as set forth in U.S. Pat. No. 4,924,011 to Denis et al. and U.S. Pat. No. 4,924,012 to Colin et al. or by the reaction of a beta-lactam and a suitably protected 10-deacetylbaccatin III or baccatin III derivative as set forth in U.S. Pat. No. 5,175,315 to Holton et al. or U.S. patent application Ser. No. 10/683,865, which application is assigned to the assignee of the present invention. 10-deacetylbaccatin III (10-DAB, 3) and baccatin III (BACC III, 4) can be separated from mixtures extracted from natural sources such as the needles, stems, bark or heartwood of numerous *Taxus* species and have the following structures.

10-DAB
(3)

BACC III
(4)

Although, much of the research towards the semi-synthesis of paclitaxel and taxotere has involved 10-deacetylbaccatin III as the starting material, other taxanes from the *Taxus* species, such as 9-dihydro-13-acetylbaccatin III (9-DHB, 5), present in the Canadian yew (*Taxus Canadensis*), cephalomannine (6), 10-deacetyl taxol (10-DAT, 7), 7-xylosyl taxol (8), 10-deacetyl-7-xylosyl taxol (9) and a number of 7-epi-taxanes have been collected and identified.

9-DHB (5)

CEPHALOMANNINE (6)

10-DAT (7)

7-XYLOSYL TAXOL (8)

10-DEACETYL-7-XYLOSYL TAXOL (9)

As disclosed in U.S. patent application Ser. No. 10/695,416, which application is assigned to the assignee of the present invention, U.S. Pat. Nos. 6,576,777 and 6,222,053 to Zamir et al. and U.S. Pat. Nos. 6,175,023 and 6,179,981 to Liu et al., docetaxel and paclitaxel (and suitable starting materials for the synthesis thereof) may also be prepared semi-synthetically from 9-dihydro-13-acetylbaccatin III.

In addition, U.S. Pat. Nos. 5,202,448 and 5,256,801 to Carver et al., U.S. Pat. No. 5,449,790 to Zheng et al. and U.S. Pat. No. 6,281,368 to McChesney et al. disclose processes for converting certain taxanes (namely, paclitaxel, cephalomannine, 10-deacetyl taxol and certain 10-deacetyl taxol derivatives) present in partially purified taxane mixtures into 10-deacetylbaccatin III and baccatin III, which may subsequently be utilized in the foregoing semi-synthetic pathways.

Although there have been many advances in the field, there remains a need for new and improved processes for the preparation of taxane intermediates and their conversion to paclitaxel and docetaxel, and also for the preparation of such taxane intermediates from crude and partially purified mixtures comprising a plurality of taxanes. The present invention addresses these needs and provides further related advantages.

BRIEF SUMMARY OF THE INVENTION

In brief, the present invention relates to the semi-synthesis of taxane intermediates useful in the preparation of paclitaxel and docetaxel, in particular, the semi-synthesis of protected taxane intermediates. As set forth below, each of the disclosed processes comprises a novel single combined step of cleaving the ester linkage at the C-13 position of a taxane having an ester linkage at the C-13 position and attaching a side chain to the C-13 position of the taxane to yield a C-13 protected taxane intermediate.

For example, in a first embodiment, the present invention provides a process for attaching a side chain to a taxane having an ester linkage at the C-13 position, the process comprising a single combined step of cleaving the ester linkage at the C-13 position of the taxane and attaching the side chain to the C-13 position of the taxane to yield a C-13 protected taxane intermediate, wherein the single combined step comprises combining the taxane with both a base and a precursor to the side chain, and wherein the precursor to the side chain is selected from the group consisting of beta-lactams, oxazolidines and oxazolines.

In a more specific embodiment of the foregoing, the precursor to the side chain is a beta-lactam. More specifically, the beta-lactam has the structure:

wherein $R_1$ is a hydroxy group, protected hydroxy group, thiol group, or protected thiol group; $R_2$ is alkyl, alkenyl, alkynyl, or aryl where $R_2$ is optionally substituted with one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl, where the alkoxy portion contains 1 to 15 carbons, aryloxycarbonyl, where the aryloxy portion contains 6 to 20 carbon, or heteroarylcarbonyl, where the heteroaryl portion contains 3 to 15 carbon atoms; and $R_3$ is hydrogen, $C_1$-$C_6$ alkyl or aryl where $R_3$ is optionally substituted with one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl, where the alkoxy portion contains 1 to 15 carbons, aryloxycarbonyl, where the aryloxy portion contains 6 to 20 carbon, or heteroarylcarbonyl, where the heteroaryl portion contains 3 to 15 carbon atoms. In a specific embodiment, the beta-lactam has the structure:

In another more specific embodiment, the base is selected from the group consisting of DMAP, TEA, LiOH, Li-t-OBu, n-BuLi, LiH, $LiBH_4$, K-t-OBu, NaH, $NaBH_4$ and mixtures of any two or more of the foregoing.

In a further embodiment, the single combined step further comprises combining the taxane with a metal halide, wherein the metal is selected from the group consisting of Group I, II and III metals and transition metals. More specifically, the metal halide is calcium chloride or zinc chloride.

In another further embodiment, the taxane further has a hydroxy group at the C-7 position, and the process further comprises a step, of protecting the hydroxy group at the C-7 position of the taxane prior to the single combined step.

In a more specific embodiment of the foregoing, the step of protecting the hydroxy group at the C-7 position of the taxane comprises combining the taxane with a base and a hydroxy-protecting group in an organic solvent, wherein the base is selected from the group consisting of DMAP, pyridine, TEA, LiOH, Li-t-OBu, n-BuLi, K-t-OBu and mixtures of any two or more of the foregoing, such as a mixture of n-BuLi/K-t-OBu, and the hydroxy-protecting group is selected from the group consisting of alkylating agents and acylating agents. More specifically, the hydroxy-protecting group is selected from the group consisting of tert-butoxycarbonyl, benzyloxycarbonyl, 2,2,2-trichloroethoxycarbonyl, dichloroacetyl and acetyl. In specific embodiments, the base is DMAP and the hydroxy-protecting group is tert-butoxycarbonyl or dichloroacetyl.

In yet another further embodiment, taxane further has a hydroxy group at the C-10 position, and the step of protecting the hydroxy group at the C-7 position of the taxane further comprises protecting the hydroxy group at the C-10 position of the taxane.

In another further embodiment, the taxane further has a hydroxy group at the C-9 position, and the process further comprises a step of oxidizing the hydroxy group at the C-9 position of the taxane following the step of protecting the hydroxy group at the C-7 position of the taxane and prior to the single combined step.

In a more specific embodiment of the foregoing, the step of oxidizing the hydroxy group at the C-9 position of the taxane comprises combining the taxane with an oxidizing agent selected from the group consisting of 4-(dimethylamino)pyridinium chlorochromate, pyridinium chlorochromate, chromium (IV) oxide-silica gel, chromium (IV) oxide-acetic acid, bromine, dimethyl sulfoxide-dicyclohexylcarbodiimide, and manganese dioxide with dichloro(p-cymene)-ruthenium (II). In a specific embodiment, the oxidizing agent is chromium (IV) oxide-silica gel.

The foregoing processes may be utilized to convert a number of different taxanes, including 9-dihydro-13-acetylbaccatin III, paclitaxel, 10-deacetylbaccatin III, baccatin III, cephalomannine, 10-deacetyl taxol, 7-xylosyl taxol, 10-deacetyl-7-xylosyl taxol and mixtures thereof, into protected taxane intermediates, that can be used to further synthesize paclitaxel and docetaxel.

For example, in a second embodiment, the present invention provides a process for preparing paclitaxel or docetaxel from 9-dihydro-13-acetylbaccatin III, the process comprising the steps of:

(1) protecting the hydroxy group at the C-7 position of the 9-dihydro-13-acetylbaccatin III to yield a first C-7 protected 9-dihydro-13-acetylbaccatin III derivative;

(2) oxidizing the hydroxy group at the C-9 position of the first C-7 protected 9-dihydro-13-acetylbaccatin III derivative to yield a second C-7 protected 13-acetylbaccatin III derivative;

(3) cleaving the ester linkage at, and attaching a side chain to, the C-13 position of the second C-7 protected 13-acetylbaccatin III derivative to yield a C-13 protected taxane intermediate; and

(4) converting the C-13 protected taxane intermediate to paclitaxel or docetaxel, wherein the step of cleaving the ester linkage at, and attaching a side chain to, the C-13 position of the second C-7 protected 13-acetylbaccatin III derivative comprises combining the second C-7 protected 13-acetylbaccatin III derivative with both a base and a precursor to the side chain, and wherein the precursor to the side chain is selected from the group consisting of beta-lactams, oxazolidines and oxazolines.

As above, in a more specific embodiment, the precursor to the side chain is a beta-lactam. More specifically, the beta-lactam has the structure:

wherein $R_1$ is a hydroxy group, protected hydroxy group, thiol group, or protected thiol group; $R_2$ is alkyl, alkenyl, alkynyl, or aryl where $R_2$ is optionally substituted with one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl, where the alkoxy portion contains 1 to 15 carbons, aryloxycarbonyl, where the aryloxy portion contains 6 to 20 carbon, or heteroarylcarbonyl, where the heteroaryl portion contains 3 to 15 carbon atoms; and $R_3$ is hydrogen, $C_1$-$C_6$ alkyl or aryl where $R_3$ is optionally substituted with one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl, where the alkoxy portion contains 1 to 15 carbons, aryloxycarbonyl, where the aryloxy portion contains 6 to 20 carbon, or heteroarylcarbonyl, where the heteroaryl portion contains 3 to 15 carbon atoms. In a specific embodiment, the beta-lactam has the structure:

The aforementioned processes may also be utilized to convert a mixture of taxanes, such as a plurality of taxanes present in a crude taxane extract or in a waste taxane solution, into a mixture of protected taxane intermediates, that can be used to further synthesize paclitaxel and docetaxel. Representative waste taxane solutions may comprise (1) pooled waste stream fractions collected following the chromatographic separation and collection of paclitaxel enriched fractions from a crude or partially purified taxane extract, and/or (2) pooled waste mother liquors collected following the recrystallization of a crude or partially purified taxane extract.

For example, in a third embodiment, the present invention provides a process for preparing paclitaxel or docetaxel from an initial mixture of taxanes, wherein the initial mixture comprises 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol, the process comprising the steps of:

(1) protecting the hydroxy group at the C-7 position of each taxane in the initial mixture having a hydroxy group at the C-7 position to yield a first intermediate mixture of C-7 protected taxanes;

(2) oxidizing the hydroxy group at the C-9 position of each taxane in the first intermediate mixture having a hydroxy group at the C-9 position to yield a second intermediate mixture of C-7 protected taxanes;

(3) cleaving the ester linkage at the C-13 position of each taxane in the second intermediate mixture having an ester linkage at the C-13 position and attaching a side chain to the C-13 position of each taxane in the second intermediate mixture to yield a mixture of C-13 protected taxane intermediates; and

(4) converting the C-13 protected taxane intermediates to paclitaxel or docetaxel, wherein the step of cleaving the ester linkage at the C-13 position of each taxane in the second intermediate mixture having an ester linkage at the C-13 position and attaching a side chain to the C-13 position of each taxane in the second intermediate mixture comprises combining the second intermediate mixture with both a base and a precursor to the side chain, and wherein the precursor to the side chain is selected from the group consisting of beta-lactams, oxazolidines and oxazolines.

Again, as above, in a more specific embodiment, the precursor to the side chain is a beta-lactam. More specifically, the beta-lactam has the structure:

wherein $R_1$ is a hydroxy group, protected hydroxy group, thiol group, or protected thiol group; $R_2$ is alkyl, alkenyl, alkynyl, or aryl where $R_2$ is optionally substituted with one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl, where the alkoxy portion contains 1 to 15 carbons, aryloxycarbonyl, where the aryloxy portion contains 6 to 20 carbon, or heteroarylcarbonyl, where the heteroaryl portion contains 3 to 15 carbon atoms, and $R_3$ is hydrogen, $C_1$-$C_6$ alkyl or aryl where $R_3$ is optionally substituted with one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl, where the alkoxy portion contains 1 to 15 carbons, aryloxycarbonyl, where the aryloxy portion contains 6 to 20 carbon, or heteroarylcarbonyl, where the heteroaryl portion contains 3 to 15 carbon atoms. In a specific embodiment, beta-lactam has the structure:

In a further embodiment, the step of protecting the hydroxy group at the C-7 position of each taxane in the initial mixture further comprises protecting the hydroxy group at the C-10 position of each taxane in the initial mixture having a hydroxy group at the C-10 position.

In other further embodiments, the initial mixture comprises: (1) 9-dihydro-13-acetylbaccatin III, and at least two additional taxanes selected from paclitaxel, 10-deacetylbaccatin III, baccatin III, cephalomannine, 10-deacetyl taxol, 7-xylosyl taxol and 10-deacetyl-7-xylosyl taxol; (2) 9-dihydro-13-acetylbaccatin III, and at least three additional taxanes selected from paclitaxel, 10-deacetylbaccatin III, baccatin III, cephalomannine, 10-deacetyl taxol, 7-xylosyl taxol and 10-deacetyl-7-xylosyl taxol; or (3) 9-dihydro-13-acetylbaccatin III, paclitaxel, 10-deacetylbaccatin III, baccatin III, cephalomannine, 10-deacetyl taxol, 7-xylosyl taxol and 10-deacetyl-7-xylosyl taxol.

In other further embodiments, the initial mixture of taxanes is a waste taxane solution comprising one or more of the following: (1) pooled waste stream fractions collected during a chromatographic separation of a crude or partially purified taxane extract; and (2) pooled waste mother liquors collected during a recrystallization of a crude or partially purified taxane extract. In two specific embodiments, the waste taxane solution comprises: (1) pooled waste stream fractions collected during a chromatographic separation of a crude taxane extract; and (2) pooled waste stream fractions collected during chromatographic separations of both crude and partially purified taxane extracts and pooled waste mother liquors collected during recrystallizations of both crude and partially purified taxane extracts.

In a fourth embodiment, the present invention provides compounds of the formula:

wherein $R_{P1}$ and $R_{P2}$ are the same or different and each represent a hydroxy-protecting group, and wherein $R_{P2}$ is selected from the group consisting of t-BOC, CBZ, TROC and dichloroacetyl when $R_{P1}$ is acetyl, and $R_{P1}$ is selected from the group consisting of t-BOC, CBZ, TROC, acetyl and dichloroacetyl when $R_{P2}$ is t-BOC. In a specific embodiment, $R_{P2}$ is t-BOC and $R_{P1}$ is acetyl. In another more specific embodiment, $R_{P1}$ and $R_{P2}$ are the same and are selected from the group consisting of t-BOC, CBZ, TROC and dichloroacetyl.

In a fifth embodiment, the present invention provides compounds of the formula:

wherein $R_{P1}$ and $R_{P2}$ are the same or different and each represent a hydroxy-protecting group, and wherein $R_{P2}$ is selected from the group consisting of t-BOC, CBZ, TROC and dichloroacetyl when $R_{P1}$ is acetyl, and $R_{P1}$ is selected from the group consisting of t-BOC, CBZ, TROC, acetyl and dichloroacetyl when $R_{P2}$ is t-BOC. In a specific embodiment, $R_{P2}$ is t-BOC and $R_{P1}$ is acetyl. In another more specific embodiment, $R_{P1}$ and $R_{P2}$ are the same and are selected from the group consisting of t-BOC, CBZ, TROC and dichloroacetyl.

These and other aspects of the invention will be apparent upon reference to the attached figures and following detailed description.

DETAILED DESCRIPTION OF THE INVENTION

I. Definitions

As used herein, the following terms have the following meanings.

"Silica matrix" is a solid media containing a silicate which is used as an adsorbent or column material in chromatographic separations, including (but not limited to) ordinary silica, Florisil, porous silica gels or any physical formulation of a silicate for use in chromatographic procedures.

"Taxane-containing material" refers to selected parts of a plant, plant tissues, cell cultures, microorganisms or extracts with extractable taxanes, including paclitaxel, 10-deacetylbaccatin III (10-DAB), baccatin III (BACC III), 9-dihydro-13-acetylbaccatin III (9-DHB), cephalomannine, 10-deacetyl taxol (10-DAT), 7-xylosyl taxol and 10-deacetyl-7-xylosyl taxol.

"Crude taxane extract" refers to a composition obtained from a taxane-containing material by treating the taxane-containing material with at least one solvent.

"Partially purified taxane extract" refers to a paclitaxel enriched composition obtained from the chromatographic separation and/or recrystallization of a crude or partially purified taxane extract.

"Waste stream fractions" refers to fractions collected following the chromatographic separation and collection of paclitaxel enriched fractions from a crude or partially purified taxane extract by, for example, the process of U.S. Pat. No. 6,136,989.

"Waste mother liquors" refers to mother liquors collected following the recrystallization of a crude or partially purified taxane extract by, for example, the process of U.S. Pat. No. 6,136,989.

"Hydroxy-protecting group" refers to a readily cleavable group bonded to the oxygen of a hydroxy (—OH) group. Examples of hydroxy-protecting groups include, without limitation, formyl, acetyl (Ac), benzyl (PhCH$_2$), 1-ethoxyethyl (EE), methoxymethyl (MOM), (methoxyethoxy)methyl (MEM), (p-methoxyphenyl)methoxymethyl (MPM), tert-butyldimethylsilyl (TBS), tert-butyldiphenylsilyl (TBPS), tert-butoxycarbonyl (tBoc, t-Boc, tBOC, t-BOC), tetrahydropyranyl (THP), triphenylmethyl (Trityl, Tr), 2-methoxy-2-methylpropyl, benzyloxycarbonyl (Cbz), dichloroacetyl, trichloroacetyl (OCCCl$_3$), 2,2,2-trichloroethoxycarbonyl (Troc), benzyloxymethyl (BOM), tert-butyl (t-Bu), triethylsilyl (TES), trimethylsilyl (TMS), triisopropylsilyl (TIPS), propionyl, isopropionyl, pivalyl, dimethylisopropylsilyl, diethylisopropylsilyl, methyldiphenylsilyl, dimethylphenylsilyl, tert-butyldiphenylsilyl, tribenzylsilyl, triphenylsilyl, trichloroethoxycarbonyl, benzyl, para-nitrobenzyl, para-methoxybenzyl, benzoyl, methoxyethyl, para-methoxyphenyl, tetrahydrofuranyl, alkylsulfonyl and arylsulfonyl. The related term "protected hydroxy group" refers to a hydroxy group that is bonded to a hydroxy-protecting group. General examples of protected hydroxy groups include, without limitation, —O-alkyl, —O-acyl, acetal, and —O-ethoxyethyl, where some specific protected hydroxy groups include, formyloxy, acetoxy, propionyloxy, chloroacetoxy, bromoacetoxy, dichloroacetoxy, trichloroacetoxy, trifluoroacetoxy, methoxyacetoxy, phenoxyacetoxy, benzoyloxy, benzoylformoxy, p-nitro benzoyloxy, ethoxycarbonyloxy, methoxycarbonyloxy, propoxycarbonyloxy, 2,2,2-trichloroethoxycarbonyloxy, benzyloxycarbonyloxy, tert-butoxycarbonyloxy, 1-cyclopropylethoxycarbonyloxy, phthaloyloxy, butyryloxy, isobutyryloxy, valeryloxy, isovaleryloxy, oxalyoxy, succinyloxy and pivaloyloxy, phenylacetoxy, phenylpropionyloxy, mesyloxy, chlorobenzoyloxy, para-nitrobenzoyloxy, para-tert-butyl benzoyloxy, caproyloxy, acryloyloxy, methylcarbamoyloxy, phenylcarbamoyloxy, naphthylcarbamoyloxy, and the like. Hydroxy-protecting groups and protected hydroxy groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

"Thiol-protecting group" refers to a readily cleavable group bonded to the sulfur of a thiol (—SH) group. Examples of thiol-protecting groups include, without limitation, triphenylmethyl (trityl, Trt), acetamidomethyl (Acm), benzamidomethyl, 1-ethoxyethyl, benzoyl, and the like. The related term "protected thiol group" refers to a thiol group that is bonded to a thiol-protecting group. General examples of protected thiol groups include, without limitation, —S-alkyl (alkylthio, e.g., $C_1$-$C_{10}$alkylthio), —S-acyl (acylthio), thioacetal, —S-aralkyl (aralkylthio, e.g., aryl($C_1$-$C_4$)alkylthio), where some specific protected thiols groups include methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio and cyclohexylthio, benzylthio, phenethylthio, propionylthio, n-butyrylthio and iso-butyrylthio. Thiol-protecting groups and protected thiol groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

The following Table shows the chemical structure of some protecting groups, as well as nomenclature used to identify those chemical structures.

meant to include n-butyl, sec-butyl, isobutyl and t-butyl; propyl includes n-propyl and isopropyl.

"Alkenyl" refers to an alkyl group having at least one site of unsaturation, i.e., at least one double bond.

"Alkynyl" refers to an alkyl group having at least one triple bond between adjacent carbon atoms.

"Alkoxy" and "alkoxyl" both refer to moieties of the formula —O-alkyl. Examples include methoxy, ethoxy, propoxy, isopropoxy, cyclopropyloxy, cyclohexyloxy and the like. Lower-alkoxy refers to groups containing one to four carbons. The analogous term "aryloxy" refers to moieties of the formula —O-aryl.

"Acyl" refers to moieties of the formula —C(=O)-alkyl. One or more carbons in the acyl residue may be replaced by nitrogen, oxygen or sulfur as long as the point of attachment to the parent remains at the carbonyl. Examples include

TABLE 1

"Alkyl" refers to a hydrocarbon structure wherein the carbons are arranged in a linear, branched, or cyclic manner, including combinations thereof. Lower alkyl refers to alkyl groups of from 1 to 5 carbon atoms. Examples of lower alkyl groups include methyl, ethyl, propyl, isopropyl, butyl, s- and t-butyl and the like. "Cycloalkyl" is a subset of alkyl and includes cyclic hydrocarbon groups of from 3 to 13 carbon atoms. Examples of cycloalkyl groups include cyclopropyl, cyclobutyl, cyclopentyl, norbornyl, adamantyl and the like. When an alkyl residue having a specific number of carbons is named, all geometric isomers having that number of carbons are intended to be encompassed; thus, for example, "butyl" is acetyl, benzoyl, propionyl, isobutyryl, t-butoxycarbonyl, benzyloxycarbonyl and the like. Lower-acyl refers to groups containing one to four carbons.

"Aryl" refers to phenyl or naphthyl. Substituted aryl refers to mono- and poly-substituted phenyl or naphthyl. Exemplary substituents for aryl include one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl where the alkoxy portion contains 1 to 15 carbons, aryloxycarbonyl where the aryloxy portion contains 6 to 20 carbon, or heteroarylcarbonyl where the heteroaryl portion contains 3 to 15 carbon atoms.

"Heteroaryl" refers to a 5- or 6-membered heteroaromatic ring containing 1-3 heteroatoms selected from O, N, or S; a bicyclic 9- or 10-membered heteroaromatic ring system containing 0-3 heteroatoms selected from O, N, or S; or a tricyclic 13- or 14-membered heteroaromatic ring system containing 0-3 heteroatoms selected from O, N, or S. Exemplary aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Leaving group" refers to a chemical moiety that may be displaced during a substitution or elimination reaction. Exemplary leaving groups include halogen (e.g., bromide and chloride) and tosyl.

"Halogen" refers to fluoro, chloro, bromo or iodo.

II. Process for Preparing C-13 Protected Taxane Intermediates

As noted above, the present invention relates to the semi-synthesis of taxane intermediates useful in the preparation of paclitaxel and docetaxel, in particular, the semi-synthesis of protected taxane intermediates.

As further noted above, each of the disclosed semi-synthetic processes comprises a novel single combined step of cleaving the ester linkage at the C-13 position of a taxane having an ester linkage at the C-13 position and attaching a side chain to the C-13 position of the taxane to yield a C-13 protected taxane intermediate. For example, the present invention provides a process for attaching a side chain to a taxane having an ester linkage at the C-13 position, the process comprising a single combined step of cleaving the ester linkage at the C-13 position of the taxane and attaching the side chain to the C-13 position of the taxane to yield a C-13 protected taxane intermediate, wherein the single combined step comprises combining the taxane with both a base and a precursor to the side chain. As noted above, the precursor to the side chain is selected from the group consisting of beta-lactams, oxazolidines and oxazolines.

In further embodiments, the foregoing process may further comprise a protection step to protect a hydroxy group, if present, at the C-7 position of the taxane, and an oxidation step to oxidize a hydroxy group, if present, at the C-9 position of the taxane. In yet a further embodiment, the foregoing protection step further comprises protecting a hydroxy group, if present, at the C-10 position of the taxane.

In general, the foregoing protection, oxidation, cleavage and attachment steps comprise the following methods.

General Method of Protection

The hydroxy groups at the C-7 and/or C-10 positions of a taxane can be selectively protected using any of a variety of hydroxy protecting groups, such as acetal, ketal, silyl, and removable acyl protecting groups. For example, the C-7 and/or C-10 hydroxy group may be silylated using any of a variety of common silylating agents including, but not limited to, tri(hydrocarbonyl)silyl halides and tri(hydrocarbonyl)silyl triflates. The hydrocarbonyl moieties of these compounds may be substituted or unsubstituted and preferably are substituted or unsubstituted alkyl or acyl. More specifically, the C-7 and/or C-10 hydroxy group can be selectively silylated, for example, using silylating agents such as tribenzylsilyl chloride, trimethylsilyl chloride, triethylsilyl chloride, dimethylisopropylsilyl chloride, dimethylphenylsilyl chloride and the like. Alternatively, selective acylation of the C-7 and/or C-10 hydroxy group can be achieved using any of a variety of common acylating agents, but not limited to substituted and unsubstituted carboxylic acid derivatives, e.g., carboxylic acid halides, anhydrides, dicarbonates, isocyanates and haloformates. More specifically, the C-7 and/or C-10 hydroxy group can be selectively acylated, for example, with di-tert-butyl dicarbonate, dibenzyl dicarbonate, diallyl dicarbonate, 2,2,2-trichloroethyl chloroformate, benzyl chloroformate, dichloroacetyl chloride or acetyl chloride, or another common acylating agent.

In the present invention, these protecting reactions are carried out in the presence of a base, such as, for example, Li-t-OBu, K-t-OBu, n-BuLi, LiOH, pyridine, DMAP, TEA, or a mixture of any two or more of the foregoing, such as a mixture of n-BuLi/K-t-OBu.

Exemplary reaction conditions are as follows: a taxane, or a mixture of taxanes, is dissolved in an organic solvent, such as anhydrous DCM (dichloromethane) or THF (tetrahydrofuran) or DMF (dimethyl formamide) or DMSO (dimethyl sulfoxide) or acetonitrile under an argon atmosphere at low temperature. To this solution is added DMAP (dimethylaminopyridine) or any other lithium or potassium base, such as Li-t-OBu, K-t-OBu, n-BuLi, a mixture of n-BuLi/K-t-OBu, or LiOH, followed by an acylating agent, such as di-tert-butyl dicarbonate, or an alkylating agent, such as triethyl silyl chloride or any other chloride containing a hydroxy-protecting group. The mixture is left at low to room temperature until complete consumption of the starting material, as visualized by TLC. The mixture is then quenched with cold water and extracted thrice with DCM. The organic layer is washed with water and then with brine to remove unwanted salts. The organic layer may then be dried and evaporated under vacuum, and the residue recrystallized or column chromatographed with DCM/EtOAc mixtures to afford a C-7 and/or C-10 protected taxane or a mixture of C-7 and/or C-10 protected taxanes.

Following protection of the hydroxy groups at the C-7 and/or C-10 positions of a taxane using the foregoing process, compounds of the following formula may be prepared:

wherein $R_{P1}$ and $R_{P2}$ are the same or different and each represent a hydroxy-protecting group, and wherein $R_{P2}$ is selected from the group consisting of t-BOC, CBZ, TROC and dichloroacetyl when $R_{P1}$ is acetyl, and $R_{P1}$ is selected from the group consisting of t-BOC, CBZ, TROC, acetyl and dichloroacetyl when $R_{P2}$ is t-BOC. In a more specific embodiment, $R_{P2}$ is t-BOC and $R_{P1}$ is acetyl. In another more specific embodiment, $R_{P1}$ and $R_{P2}$ are the same and are selected from the group consisting of t-BOC, CBZ, TROC and dichloroacetyl.

General Method of Oxidation

A C-7 protected taxane may be selectively oxidized at the C-9 position using various oxidizing agents, such as 4-(dimethylamino)pyridinium chlorochromate, pyridinium chlorochromate, chromium (IV) oxide-silica gel, chromium (IV) oxide-acetic acid (Fieser reagent) or acidic media, bromine, dimethyl sulfoxide-dicyclohexylcarbodiimide, and manganese dioxide with dichloro(p-cymene)-ruthenium (II).

For example, a C-7 protected taxane, or a mixture of C-7 protected taxanes, is dissolved in an organic solvent and treated with an oxidant at low to room temperature conditions. The reaction is stirred until all the starting material is consumed, as evidenced by TLC. The reaction is then worked up as usual to yield an oxidized C-7 protected taxane or a mixture of oxidized C-7 protected taxanes. Such product can be further purified by column chromatography or crystallized from a suitable solvent.

Following oxidation of the hydroxy group at the C-9 position of a taxane using the foregoing process, compounds of the following formula may be prepared:

wherein $R_{P1}$ and $R_{P2}$ are the same or different and each represent a hydroxy-protecting group, and wherein $R_{P2}$ is selected from the group consisting of t-BOC, CBZ, TROC and dichloroacetyl when $R_{P1}$ is acetyl, and $R_{P1}$ is selected from the group consisting of t-BOC, CBZ, TROC, acetyl and dichloroacetyl when $R_{P2}$ is t-BOC. In a more specific embodiment, $R_{P2}$ is t-BOC and $R_{P1}$ is acetyl. In another more specific embodiment, $R_{P1}$ and $R_{P2}$ are the same and are selected from the group consisting of t-BOC, CBZ, TROC and dichloroacetyl.

General Method of Cleavage and Attachment

An ester linkage at the C-13 position of a taxane may be cleaved and a side chain may be attached to the C-13 position of the taxane in a single combined step by combining the taxane with both a base and a precursor to the side chain. Representative bases include DMAP, TEA, LiOH, Li-t-OBu, n-BuLi, LiH, LiBH$_4$, K-t-OBu, NaH, NaBH$_4$ or a mixture of any two or more of the foregoing. In addition, the single combined step may further comprise combining the taxane with a metal halide, wherein the metal halide is selected from the group consisting of Group I, II and III metals and transition metals. Representative metal halides include, for example, calcium chloride and zinc chloride. Representative precursors to the side chains are described in more detail below, and include beta-lactams having the structure:

For example, a taxane having an ester linkage at the C-13 position, or a mixture of taxanes, is dissolved in an organic solvent under an argon temperature at low temperature, for example, −78° C. to room temperature. To this solution is added a base, such as DMAP, TEA, LiOH, Li-t-OBu, n-BuLi, LiH, LiBH$_4$, K-t-OBu, NaH, NaBH$_4$ or a mixture of any two or more of the foregoing, followed by a solution of a beta-lactam. The mixture is left to react at low to room temperature until complete consumption of the starting material, as visualized by TLC. A solution of an acid, such as AcOH, in an organic solvent is added to the mixture, and the mixture is partitioned between saturated aqueous sodium hydrogen carbonate and mixtures of DCM and ethyl acetate. The combined organic extracts are dried and evaporated to give the crude C-13 beta-lactam protected taxane intermediate, which can be further purified by column chromatography or crystallized from a suitable solvent.

III. Taxane Starting Material

As noted above, the processes of the present invention may be utilized to convert taxanes, and mixtures of taxanes, into protected taxane intermediates, that can be used to further synthesize paclitaxel and docetaxel. Representative taxanes for use in the disclosed processes include 9-dihydro-13-acetylbaccatin III, paclitaxel, 10-deacetylbaccatin III, baccatin III, cephalomannine, 10-deacetyl taxol, 7-xylosyl taxol and 10-deacetyl-7-xylosyl taxol, each of which contain the following baccatin molecular framework:

wherein $R_A$, $R_B$, $R_C$ and $R_D$ represent substituents which vary between the taxanes. More specifically, $R_A$ is —OH, —OAc, N-(2-methyl-2-butenoyl)-(2R,3S)-3-phenylisoserine or N-benzoyl-(2R,3S)-3-phenylisoserine, $R_B$ is —OH or —OAc, $R_C$ is —OH or =O, and $R_D$ is —OH or xylosyl. For example, when $R_A$ is —OAc, $R_B$ is —OAc, $R_C$ is —OH and $R_D$ is —OH, the foregoing structure represents 9-dihydro-13-acetylbaccatin III, and when $R_A$ is —OH, $R_B$ is —OAc, $R_C$ is =O and $R_D$ is —OH, the foregoing structure represents baccatin III.

In certain embodiments, the taxanes utilized in the processes of the present invention may be purified or partially purified taxanes. Such purified and partially purified taxanes may be obtained by any of a number of different methods well known in the art. For example, 9-dihydro-13-acetylbaccatin III can be obtained by the methods described in Gunawardana et al., J. Nat. Prod. 55:1686 (1992); U.S. Pat. No. 5,530,020 to Gunawardana et al.; Zamir et al., Can. J. Chem. 73: 655 (1995); and U.S. Pat. No. 6,229,027 to Liu, which references are incorporated herein by reference in their entireties.

In other embodiments, the mixture of taxane utilized in the processes of the present invention may be a plurality of taxanes present in a crude taxane extract or in a waste taxane solution. In this way, the disclosed processes may be utilized for high yield and large scale conversion of taxanes present in a waste taxane solution into beta-lactam protected taxane intermediates, that can be used to further synthesize paclitaxel and docetaxel. Such waste taxane solutions may comprise (1) pooled waste stream fractions collected following the chromatographic separation and collection of paclitaxel enriched fractions from a crude or partially purified taxane extract, and/or (2) pooled waste mother liquors collected following the recrystallization of a crude or partially purified taxane extract.

Representative waste taxane solutions may be obtained by a number of different methods, such as, for example, the methods disclosed in U.S. Pat. No. 6,136,989 to Foo et al., and other references cited therein, which patent is incorporated herein by reference in its entirety, and U.S. patent application Ser. No. 10/831,648, which application is assigned to the assignee of the present invention and is incorporated herein by reference in its entirety. A representative method of obtaining a waste taxane solution, which comprises pooled waste stream fractions, comprises the following extraction and column chromatography steps.

Starting Taxane-Containing Material

A suitable taxane-containing material is any tissue that contains a high taxane content. Examples of suitable taxane-containing material include tissues from various species of Yew plants comprising the genus *Taxus*, most preferably the roots and needles of ornamental Yew plants such as *T. canadensis, T. x media* spp *Hicksii, T. x* dark green spreader and Hill., *T. chinensis, T. wallichiana, T. cuspidata, T. globosa, T. sumatrana, T. marei* and *T. floridana*, and the bark of *T. brevifolia* or *T. yunnanensis*. Other suitable material include cultures of plant tissues obtained from a *Taxus* species.

In a typical practice, such as set forth in U.S. Pat. No. 6,139,989, the taxane-containing material is either pulverized, chipped or otherwise ground into small pieces so as to increase efficiency of a solvent extraction. The taxane-containing material may also optionally be dried. Taxane-containing cell culture, cells, microorganisms and fermentation broths will typically be concentrated prior to solvent extraction. Cells and microorganisms can be processed as whole cells or cell paste or pulver.

Extraction

The taxane-containing material may be initially extracted by contacting the material with an organic solvent, usually for a prolonged period of at least 8 hours and typically for about 3 days with or without physical agitation to promote formation of a crude organic extract containing a plurality of taxanes. The extraction may employ any of the solvent systems that are known to be used for the extraction of paclitaxel, including but not limited to, acetone, methanol, ethanol, ethyl acetate, methylene chloride, chloroform, mixtures thereof, and mixtures containing an aqueous component of up to 60%. These solvents are typically added in an amount of about 4-20 liter per kg of the taxane-containing material to prepare the crude organic extract. Reference is made for example, to U.S. Pat. No. 6,136,989 and the publications cited therein which provide a non-exclusive description of several solvent systems that may be used to prepare an organic extract containing a plurality of taxanes.

In one embodiment, the organic solvent is a polar organic solvent, typically an alcohol. For some embodiments, methanol is preferred because of its low cost, ease of removal and efficiency of taxane extraction. In one embodiment, about 6-15 liters of methanol is added for every kg of taxane-containing material to be extracted. The extraction is accelerated by agitating the taxane-containing material, for example, by stirring or percolating the methanol with the taxane-containing material for about 1-5 days at a temperature between room temperature and about 60° C., most typically at about 40° C. When the taxane-containing material contains a paclitaxel content of at least 0.005%, methanol extraction for three days as described above recovers at least 90% of the available paclitaxel from the taxane-containing material, in addition to a plurality of other taxanes, to form a crude methanol extract containing about 0.1-0.5% paclitaxel and having an overall solid content of about 0.5-5% (w/v).

The large volume of methanol extract thus obtained is optionally concentrated, typically about 10-30 fold by evaporation to obtain a methanol extract concentrate having a solid content of about 100-400 g/L.

Liquid-Liquid Extraction

The crude organic extract may be subsequently enriched for taxanes by performing 1-3 liquid-liquid extractions by mixing the organic extract with a non-miscible, organic solvent to form a two phase system wherein one phase contains the plurality of taxanes. Generally, the two phase system includes a polar phase. Optionally, the taxane-containing phase is selected and concentrated by evaporation to form a concentrated extract having a solid content of about 100-400 g/L and a paclitaxel purity of about 1-4%. In some embodiments, water is included to help remove preferentially water soluble materials and the less polar solvent is selected to remove undesirable compounds such as waxes, lipids, pigments, and sterols that are found in different amounts depending on the taxane-containing material used. Typical solvents for liquid-liquid partitioning include hexane, hexanes, and methylene chloride. Methylene chloride has generally been found to be suitable for liquid-liquid extraction of taxane-containing material especially when the solvent used for the crude organic extract is an alcohol.

The concentrated extract obtained is optionally evaporated and the residue is re-dissolved in a solvent for loading onto a silica chromatography matrix.

Other example methods of performing a liquid-liquid extraction are illustrated in U.S. Pat. Nos. 5,475,120, 5,380, 916, and 5,670,673 to Rao and references cited therein, and also in U.S. Pat. Nos. 5,618,538 and 5,480,639 to ElSohly et al. and references cited therein. These methods or variants thereof may alternatively be used in lieu of the embodiments described. Furthermore, liquid-liquid extraction may be omitted altogether when a plant extract containing high taxane levels is obtained by other methods such as for example, by intervening precipitation, crystallization or chromatography steps. One example of such a method is found in PCT Publication Nos. WO 98/07712 by Zamir et al, which uses a precipitation step immediately after obtaining an initial organic extract to obtain a paclitaxel fraction that may be about 1% or higher.

Silica Gel Column Chromatography

As further set forth in U.S. Pat. No. 6,136,989, the concentrated extract may be further purified by normal phase silica chromatography. As used herein, silica chromatography generally refers to the process of contacting a sample dissolved in a feed solvent with a silica matrix then eluting the silica matrix with an eluting solvent to obtain a fraction enriched with a desired component.

The dimensions of the first silica column are selected according to the quantity and purity of the solids to be separated. In one embodiment of a pilot scale process, about 250 grams of solids are dissolved in about 0.75 liters of feed solvent which is then chromatographed over a Silica column of about 1.5-inches×10-feet. In another embodiment, about 40-50 kg of solids are dissolved in about 100-200 liters of feed solvent, and chromatographed over a Silica column of about 18-inches×10-feet.

It has also been shown that a layer of about 1-15 cm of Celite, preferably about 2-8 cm, on top of the silica column is recommended as a column prefilter which substantially decreases the loading time of the sample. It has further been shown that the optimal eluting solvent for the Silica column should be a hexane/acetone mixture at a ratio of about 3:1 or a DCM/ethyl acetate mixture at a ratio of about 7:3. The "heart cut" fractions containing at least 2% paclitaxel are pooled and further purified, for example, according to the process set forth in U.S. Pat. No. 6,136,989. The remaining waste stream fractions, which contain a plurality of taxanes, including, paclitaxel, 10-deacetylbaccatin III (10-DAB), baccatin III (BACC III), 9-dihydro-13-acetylbaccatin III (9-DHB), cephalomannine, 10-deacetyl taxol (10-DAT), 7-xylosyl taxol and 10-deacetyl-7-xylosyl taxol are pooled into a waste taxane solution for further processing according to the present invention.

Further Purification Steps

As set forth in more detail in U.S. Pat. No. 6,139,989, the paclitaxel enriched "heart cut" fractions obtained from the foregoing chromatography step may be further purified through one or more additional chromatographic or recrystallization steps. Any waste stream fractions or waste mother liquors collected during such additional purification steps may also be pooled and added to the waste taxane solution for further processing according to the present invention.

IV. Side Chains and Precursors to the Side Chains

As noted above, the precursors to the side chains utilized in the semi-synthetic processes of the present invention are selected from the group consisting of beta-lactams, oxazolidines and oxazolines. As illustrated by the following examples and the attached figures, such precursors may be reacted with a taxane having an ester linkage at the C-13 position according to processes of the present invention in order to attach a side chain to the C-13 position of the taxane.

Representative beta-lactams include the following beta-lactams described in U.S. patent application Ser. Nos. 10/683,865 and 10/790,622, which applications are assigned to the assignee of the present invention and are incorporated herein by reference in their entireties.

U.S. patent application Ser. No. 10/683,865 (the "'865 patent") discloses beta-lactams having the structure:

wherein $R_1$ is a hydroxy group, protected hydroxy group, thiol group, or protected thiol group; $R_2$ is alkyl, alkenyl, alkynyl, or aryl where $R_2$ is optionally substituted with one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl, where the alkoxy portion contains 1 to 15 carbons, aryloxycarbonyl, where the aryloxy portion contains 6 to 20 carbon, or heteroarylcarbonyl, where the heteroaryl portion contains 3 to 15 carbon atoms; and $R_3$ is hydrogen, $C_1$-$C_6$ alkyl or aryl where $R_3$ is optionally substituted with one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl, where the alkoxy portion contains 1 to 15 carbons, aryloxycarbonyl, where the aryloxy portion contains 6 to 20 carbon, or heteroarylcarbonyl, where the heteroaryl portion contains 3 to 15 carbon atoms.

Figure 1:
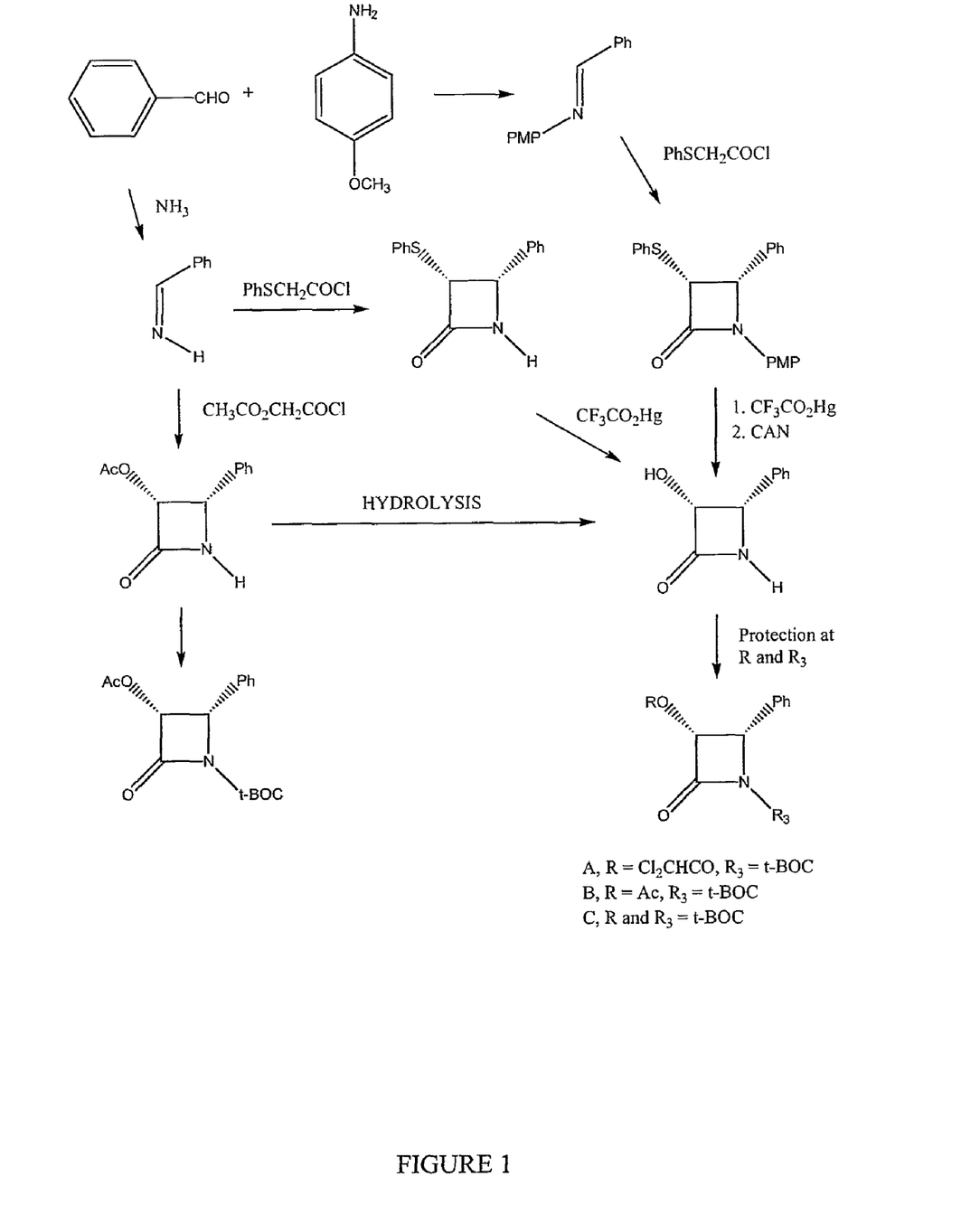
FIG. 1 illustrates several chemical routes for the preparation of beta-lactam side chains for use in the semi-synthetic processes of the present invention.

As described in the '865 patent, and as shown in FIG. 1, such beta-lactams may be prepared according to the reaction scheme:

wherein LG is a leaving group and $R_1$, $R_2$ and $R_3$ are as defined above. In addition, as further described in the '865 patent, and as shown in FIG. 1, such beta-lactams may be further converted to other beta-lactam side chains.

Figure 2:
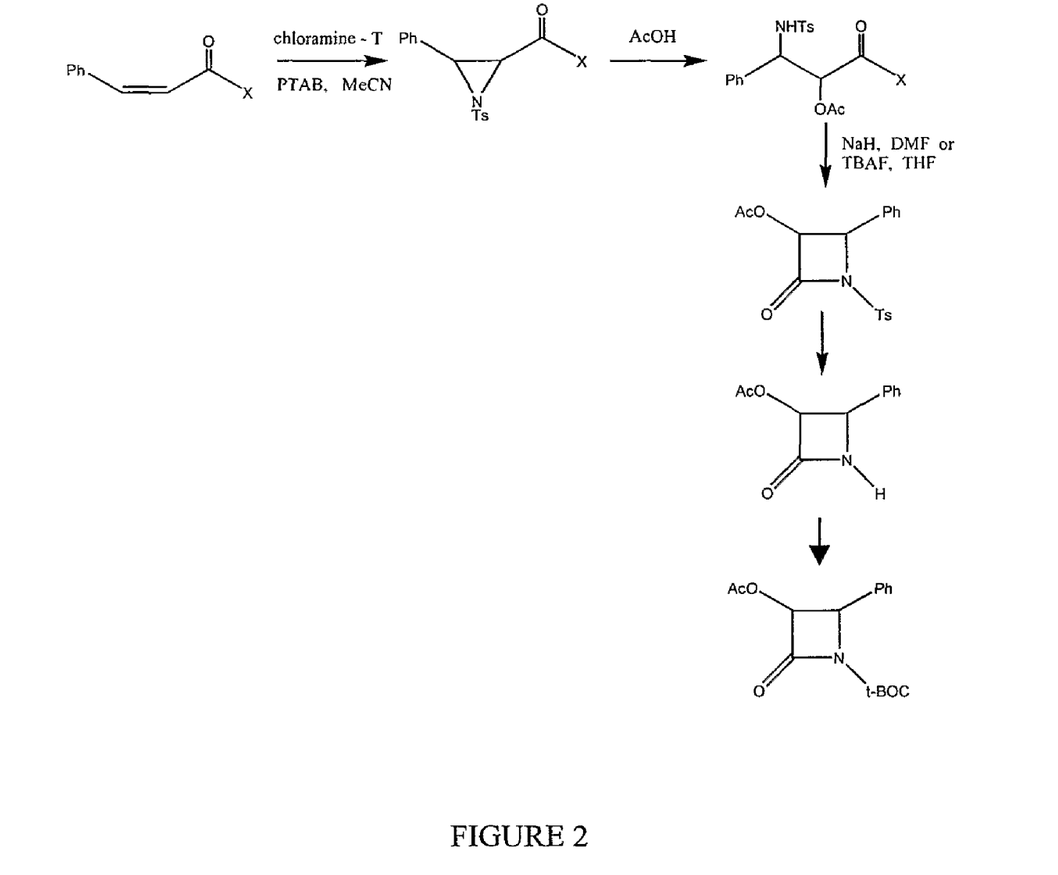
FIG. 2 illustrates a chemical route for the preparation of a beta-lactam side chain for use in the semi-synthetic processes of the present invention.

U.S. patent application Ser. No. 10/790,622 (the "'622 patent") discloses beta-lactams having the structure:

As described in the '622 patent, and as shown in FIG. 2, such beta-lactams may be prepared by (1) converting cinnamoyl halide to a cinnamoyl halide aziridine intermediate having the structure:

wherein X is halogen, (2) reacting the cinnamoyl halide aziridine intermediate with acetic acid to give an open chain cinnamoyl halide intermediate having the structure:

wherein X is halogen, and (3) converting the open chain cinnamoyl halide intermediate to the beta-lactams.

Representative oxazolidines and oxazolines are described in U.S. Pat. Nos. 6,365,750 and 6,307,071, and the references cited therein, which patents and references are incorporated herein by reference in their entireties.

V. Process for Preparing Paclitaxel or Docetaxel

As noted above, the C-13 protected taxane intermediates prepared according to the foregoing semi-synthetic processes may be utilized to further synthesize paclitaxel and docetaxel. In this way, in one embodiment, the present invention provides an overall process for preparing paclitaxel and/or docetaxel from 9-dihydro-13-acetylbaccatin III, the process comprising the steps of:

(1) protecting the hydroxy group at the C-7 position of the 9-dihydro-13-acetylbaccatin III to yield a first C-7 protected 9-dihydro-13-acetylbaccatin III derivative;

(2) oxidizing the hydroxy group at the C-9 position of the first C-7 protected 9-dihydro-13-acetylbaccatin III derivative to yield a second C-7 protected 13-acetylbaccatin III derivative;

(3) cleaving the ester linkage at, and attaching a side chain to, the C-13 position of the second C-7 protected 13-acetylbaccatin III derivative to yield a C-13 protected taxane intermediate; and (4) converting the C-13 protected taxane intermediate to paclitaxel or docetaxel, wherein the step of cleaving the ester linkage at, and attaching a side chain to, the C-13 position of the second C-7 protected 13-acetylbaccatin III derivative comprises combining the second C-7 protected 13-acetylbaccatin III derivative with both a base and a precursor to the side chain, and wherein the precursor to the side chain is selected from the group consisting of beta-lactams, oxazolidines and oxazolines.

Similarly, in another embodiment, the present invention provides an overall process for preparing paclitaxel and/or docetaxel from an initial mixture of taxanes, wherein the initial mixture comprises 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol, the process comprising the steps of:

(1) protecting the hydroxy group at the C-7 position of each taxane in the initial mixture having a hydroxy group at the C-7 position to yield a first intermediate mixture of C-7 protected taxanes;

(2) oxidizing the hydroxy group at the C-9 position of each taxane in the first intermediate mixture having a hydroxy group at the C-9 position to yield a second intermediate mixture of C-7 protected taxanes;

(3) cleaving the ester linkage at the C-13 position of each taxane in the second intermediate mixture having an ester linkage at the C-13 position and attaching a side chain to the C-13 position of each taxane in the second intermediate mixture to yield a mixture of C-13 protected taxane intermediates; and (4) converting the C-13 protected taxane intermediates to paclitaxel or docetaxel, wherein the step of cleaving the ester linkage at the C-13 position of each taxane in the second intermediate mixture having an ester linkage at the C-13 position and attaching a side chain to the C-13 position of each taxane in the second intermediate mixture comprises combining the second intermediate mixture with both a base and a precursor to the side chain, and wherein the precursor to the side chain is selected from the group consisting of beta-lactams, oxazolidines and oxazolines.

In a further embodiment of the foregoing process, the step of protecting the hydroxy group at the C-7 position of each taxane in the initial mixture further comprises protecting the hydroxy group at the C-10 position of each taxane in the initial mixture having a hydroxy group at the C-10 position.

The C-13 protected taxane intermediates may be converted to paclitaxel and docetaxel by a number of different methods, such as, for example, the methods disclosed in U.S. patent application Ser. Nos. 10/683,865 and 10/790,622, which applications are assigned to the assignee of the present invention and are incorporated herein by reference in their entireties, and U.S. Pat. Nos. 6,365,750 and 6,307,071, and the references cited therein, which patents and references are incorporated herein by reference in their entireties.

EXAMPLES

The following Examples disclose a specific process for synthesizing a C-13 beta-lactam protected taxane intermediate from 9-dihydro-13-acetylbaccatin III, and the subsequent conversion of such intermediate to docetaxel. Unless otherwise noted, all scientific and technical terms have the meanings as understood by one of ordinary skill in the art.

Example 1

Protection of C-7 Hydroxy Group

Figure 3:
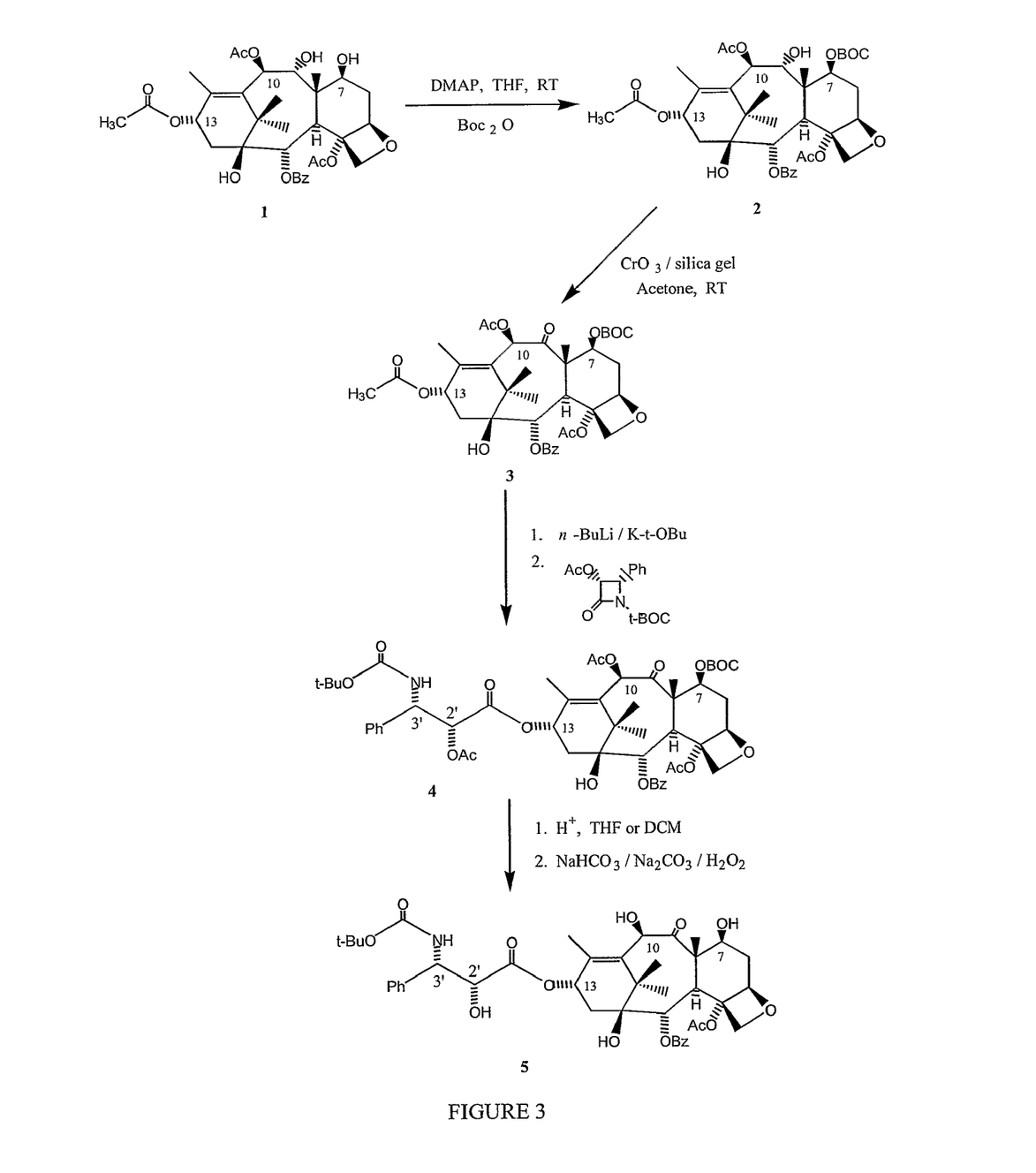
FIG. 3 illustrates a chemical route for the preparation of a C-13 beta-lactam protected taxane intermediate, and the conversion of such intermediate to docetaxel according to the present invention.

As shown in FIG. 3, a stirred solution of 9-dihydro-13-acetylbaccatin III (9-DHB), 1, in an organic solvent, such as THF, at room temperature under an argon atmosphere was treated with a hydroxy-protecting agent, such as $Boc_2O$, in the presence of a base, such as 4-(N,N-dimethylamino)pyridine. The reaction was stirred at this temperature for a period between 30 minutes to 1 hour until complete consumption of the starting materials, as evidenced by TLC. The reaction was then worked up as usual, the organic phase was washed with water twice, a saturated aqueous sodium hydrogen carbonate solution and a saturated aqueous sodium chloride solution, and then dried over anhydrous sodium sulfate. Filtration and evaporation of the solvents under reduced pressure yielded a crude first C-7 protected 9-DHB derivative, 2, which was further purified by either column chromatography or crystallization to afford a pure first C-7 protected 9-DHB derivative, 2.

Example 2

Oxidation of C-9 Hydroxy Group

As further shown in FIG. 3, the first C-7 protected 9-DHB derivative, 2, was dissolved in anhydrous acetone at room temperature and an oxidizing agent, such as chromium (IV) oxide-silica gel, was added to the mixture. After stirring the solution for 30 min to 1 h, or until complete consumption of the starting material, at a temperature in the range of about 20 to 25° C., the reaction mixture was filtered through a pad of a filtering agent, such as silica gel or celite. Evaporation of the solvent yielded a crude second C-7 protected 13-acetylbaccatin III derivative, 3, which could be used in the following synthetic step or could be further purified by either column chromatography or crystallization to afford a pure second C-7 protected 13-acetylbaccatin III derivative, 3.

Example 3

Cleavage of C-13 Ester Linkage and Attachment of a Beta-lactam Side Chain in One Pot As further shown in FIG. 3, to a solution of the second C-7 protected 13-acetylbaccatin III derivative, 3, in an organic solvent, such as freshly distilled THF, under argon atmosphere at −40 to −50° C., was added dropwise a solution of a base, such as n-BuLi, in hexanes or a mixture of n-BuLi/K-t-OBu. After stirring for 30 min to 1 hr at this temperature, a solution of a beta-lactam in anhydrous THF was added dropwise to the mixture. The solution was slowly warmed to 0° C. and kept at that temperature for an additional 1 to 3 hrs, or until complete consumption of the starting material, as evidenced by TLC, before addition of a solution of an acid in an organic solvent, such as 10% AcOH in THF. The mixture was then partitioned between saturated aqueous sodium hydrogen carbonate and mixtures of dichloromethane and ethyl acetate. Evaporation of the organic layer yielded a crude C-13 beta-lactam protected taxane intermediate, 4, which could be further purified by either column chromatography or crystallization to yield a pure C-13 beta-lactam protected taxane intermediate, 4.

Example 4

Synthesis of Docetaxel

As further shown in FIG. 3, the C-13 beta-lactam protected taxane intermediate, 4, was hydrolyzed using formic acid to remove the C-7 BOC protecting group and then with a mixture of $NaHCO_3/Na_2CO_3/H_2O_2$ to deprotect the C-2' and C-10 acetate groups to yield docetaxel, 5 as described in U.S. patent application Ser. No. 10/790,622, which application is assigned to the assignee of the present invention and is incorporated herein by reference in its entirety.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A process comprising:
preparing paclitaxel or docetaxel from 9-dihydro-13-acetylbaccatin III, through;
protecting the hydroxy group at the C-7 position of the 9-dihydro-13-acetylbaccatin III to yield a first C-7 protected 9-dihydro-13-acetylbaccatin III derivative;
oxidizing the hydroxy group at the C-9 position of the first C-7 protected 9-dihydro-13-acetylbaccatin III derivative to yield a second C-7 protected 13-acetylbaccatin III derivative;
cleaving the ester linkage at, and attaching a side chain to, the C-13 position of the second C-7 protected 13-acetylbaccatin III derivative to yield a C-13 protected taxane intermediate; and
converting the C-13 protected taxane intermediate to paclitaxel or docetaxel,
wherein the step of cleaving the ester linkage at, and attaching a side chain to, the C-13 position of the second C-7 protected 13-acetylbaccatin III derivative comprises combining the second C-7 protected 13-acetylbaccatin III derivative with both a base and a precursor to the side chain, and wherein the precursor to the side chain is selected from the group consisting of beta-lactams, oxazolidines and oxazolines.

2. The process of claim 1 wherein the precursor to the side chain is a beta-lactam.

3. The process of claim 2 wherein the beta-lactam has the structure:

wherein $R_1$ is a hydroxy group, protected hydroxy group, thiol group, or protected thiol group; $R_2$ is alkyl, alkenyl, alkynyl, or aryl where $R_2$ is optionally substituted with one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl, where the alkoxy portion contains 1 to 15 carbons, aryloxycarbonyl, where the aryloxy portion contains 6 to 20 carbon, or heteroarylcarbonyl, where the heteroaryl portion contains 3 to 15 carbon atoms; and $R_3$ is hydrogen, $C_1$-$C_6$ alkyl or aryl where $R_3$ is optionally substituted with one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl, where the alkoxy portion contains 1 to 15 carbons, aryloxycarbonyl, where the aryloxy portion contains 6 to 20 carbon, or heteroarylcarbonyl, where the heteroaryl portion contains 3 to 15 carbon atoms.

4. The process of claim 2 wherein the beta-lactam has the structure:

* * * * *

UNITED STATES PATENT AND TRADEMARK OFFICE
CERTIFICATE OF CORRECTION

PATENT NO. : 7,893,283 B2
APPLICATION NO. : 11/628428
DATED : February 22, 2011
INVENTOR(S) : Ragina Naidu Page 1 of 1

It is certified that error appears in the above-identified patent and that said Letters Patent is hereby corrected as shown below:

On the Cover Page:

In the List of References Cited at (56), in the listing of U.S. Patent Documents, the numbers and words "0,041,803 A1   11/2001   Kasitu et al." should read --2001/0041803 A1   11/2001   Kasitu et al.--

Signed and Sealed this
Twelfth Day of February, 2013

Teresa Stanek Rea
*Acting Director of the United States Patent and Trademark Office*